United States Patent
Höhn et al.

[11] Patent Number: 5,876,467
[45] Date of Patent: Mar. 2, 1999

[54] USE OF CARBOXYLIC ESTERS AS FUEL ADDITIVES OR LUBRICANT ADDITIVES AND THEIR PREPARATION

[75] Inventors: Arthur Höhn, Kirchheim, Germany; Hans Funke, Boulder, Colo.; Knut Oppenländer, Ludwigshafen, Germany; Wolfgang Günther, Mettenheim, Germany; Harald Schwahn, Wiesloch, Germany

[73] Assignee: BASF Aktiengesellschaft, Ludwigshafen, Germany

[21] Appl. No.: 687,582

[22] PCT Filed: Feb. 7, 1995

[86] PCT No.: PCT/EP95/00429

§ 371 Date: Aug. 12, 1996

§ 102(e) Date: Aug. 12, 1996

[87] PCT Pub. No.: WO95/21904

PCT Pub. Date: Aug. 17, 1995

[30] Foreign Application Priority Data

| Feb. 15, 1994 | [DE] | Germany | 44 04 742.8 |
| Sep. 19, 1994 | [DE] | Germany | 44 33 271.8 |
| Dec. 16, 1994 | [DE] | Germany | 44 44 912.7 |

[51] Int. Cl.[6] ............... C10L 1/18; C10L 1/22
[52] U.S. Cl. ............... 44/388; 44/399; 44/400
[58] Field of Search ............... 44/388, 399, 400

[56] References Cited

U.S. PATENT DOCUMENTS

| 3,307,928 | 3/1967 | Chaikivsky et al. | 44/399 |
| 3,381,022 | 4/1968 | Le Suer | 44/399 |
| 3,542,678 | 11/1970 | Bork . | |
| 3,836,469 | 9/1974 | Miller | 44/400 |
| 4,173,590 | 11/1979 | Schmidbaur et al. | 260/606.5 |

FOREIGN PATENT DOCUMENTS

| 10 807 | 5/1980 | European Pat. Off. . |
| 148 592 | 7/1985 | European Pat. Off. . |
| 19 12 517 | 10/1969 | Germany . |
| 26 58 127 | 7/1978 | Germany . |
| 29 12 489 | 10/1980 | Germany . |
| 41 34 772 | 5/1992 | Germany . |
| 33 08 882 | 9/1994 | Germany . |
| 94/13709 | 6/1994 | WIPO . |

OTHER PUBLICATIONS

Karsch et al., Z. Naturforsch, vol. 38B (11); pp. 1399–1405. date unavailable.

Primary Examiner—Jacqueline V. Howard
Attorney, Agent, or Firm—Keil & Weinkauf

[57] ABSTRACT

Carboxylic esters of the formula I $$R^1—CO—O—R^2 \qquad I,$$

where $R^1$ is an aliphatic, straight-chain or branched hydrocarbon radical having alkyl side chains and a number average molecular weight of from 250 to 5000 and $R^2$ is a straight-chain or branched hydrocarbon radical of 1 to 30 carbon atoms or a radical of the formula II

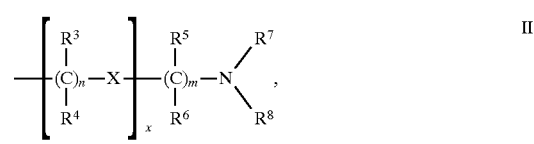

where $R^3$, $R^4$, $R^5$ and $R^6$, independently of one another, are each hyrogen, branched or straight-chain alkyl, an aromatic radical or an araliphatic radical which may also contain heteroatoms, $R^7$ and $R^8$, independently of one another, are each branched or straight-chain alkyl or an aromatic or araliphatic radical which may also contain heteroatoms, X is O, S, $NR^9$ or $PR^9$, where $R^9$ is an aliphatic or aromatic radical, n and m, independently of one another, are each from 2 to 20, and x is from 0 to 30, are used as fuel additives or lubricant additives, and fuel compositions or lubricant compositions contain these additives. Carboxylic acids or carboxylic esters are prepared by reacting polymers having at least 30 carbon atoms and at least one carbon—carbon double bond with carbon monoxide and water or an alcohol.

6 Claims, No Drawings

USE OF CARBOXYLIC ESTERS AS FUEL ADDITIVES OR LUBRICANT ADDITIVES AND THEIR PREPARATION

This application is a 371 of PCT/EP95/00429 filed Feb. 7, 1995. The present invention relates to the use of carboxylic esters of the formula I

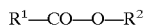

where $R^1$ is an aliphatic, straight-chain or branched hydrocarbon radical having alkyl side chains and a number average molecular weight of from 250 to 5000 and $R^2$ is a straight-chain or branched hydrocarbon radical of 1 to 30 carbon atoms or a radical of the formula II

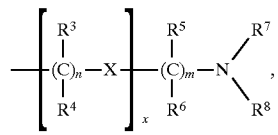

where $R^3$, $R^4$, $R^5$ and $R^6$, independently of one another, are each hydrogen, branched or straight-chain alkyl, an aromatic radical or an araliphatic radical which may also contain heteroatoms, $R^7$ and $R^8$, independently of one another, are each branched or straight-chain alkyl or an aromatic or araliphatic radical which may also contain heteroatoms, X is O, S, $NR^9$ or $PR^9$, where $R^9$ is an aliphatic or aromatic radical, among which O is preferred, n and m, independently of one another, are each from 2 to 20, preferably 2, and x is from 0 to 30, preferably 0, as fuel additives or lubricant additives, and fuel compositions or lubricant compositions containing these additives.

The present invention furthermore relates to an improved process for the preparation of carboxylic acids or carboxylic esters by reacting polymers of at least 30 carbon atoms, which carry at least one carbon—carbon double bond, with carbon monoxide and water or alcohols.

Carburettors and intake systems of gasoline engines, but also injection systems for fuel metering in gasoline and diesel engines, are increasingly being contaminated by impurities caused by dust particles from the air, uncombusted hydrocarbon residues from the combustion space and the crank case vent gases passed into the carburettor.

These residues shift the air/fuel ratio during idling and in the lower part-load range so that the mixture becomes richer and the combustion less complete and in turn the amounts of uncombusted or partially combusted hydrocarbons in the exhaust gas become larger and the gasoline consumption increases.

It is known that these disadvantages can be avoided by using fuel additives for keeping valves and carburettors or injection systems clean (cf. for example: M. Rossenbeck in Katalysatoren, Tenside, Mineralöladditive, editors J. Falbe, and U. Hasserodt, page 223, G. Thieme Verlag, Stuttgart 1978).

Today, a distinction is made between two generations on the basis of the mode of action as well as the preferred site of action of such detergent additives.

The first generation of additives was capable only of preventing the formation of deposits in the intake system but not of removing existing deposits, whereas the modern additives of the second generation can do both (keep-clean and clean-up effect) and can do so in particular because of their excellent heat stability in zones of relatively high temperature, ie. in the intake valves.

The molecular structural principle of these additives which act as detergents can be stated generally as the linking of polar structures to generally relatively high molecular weight, nonpolar or oleophilic radicals.

Compounds which are of particular interest here are those which are obtained by means of chlorine-free synthesis methods, since the use of chlorine results in the occurrence of chlorine- or chloride-containing products, which is by no means desirable today.

Such detergents, which may originate from a large number of classes of chemical substances, are generally used in combination with a carrier oil. The carrier oils have an additional wash function, often support and promote the detergents in their action and may help to reduce the required amount of detergent. The carrier oils usually used are viscous, high-boiling and in particular heat-stable liquids. They coat the hot metal surface (for example the intake valves) with a thin liquid film and thus prevent or delay the formation or deposition of decomposition products on the metal surfaces. Suitable carrier oils are, for example, high-boiling, refined mineral oil fractions, as well as synthetic liquids, such as oil-soluble adducts of alkylene oxides with alcohols.

Owing to the frequently only small detergent effect of the compounds used as carrier liquids, and a correspondingly small contribution to the overall performance of an additive package with regard to detergency, the saving of necessary detergents is not optimum and the carrier oils themselves must be used in relatively high doses. Usually, such carrier oils can by no means render the use of detergents unnecessary.

It is an object of the present invention to provide a fuel additive or lubricant additive which can be used as a carrier oil and has a pronounced detergent effect.

EP-A-148 592 relates to the preparation of carboxylic esters from polymers which carry a carbon—carbon double bond, with carbon monoxide and an alcohol in the presence of a protic acid and of a catalyst which contains at least one of the metals palladium, rhodium, ruthenium, iridium and cobalt, and copper. The products are detected by IR spectroscopy. The conversion or selectivity of this reaction is not evident from the data in the publication. When the experiments described were repeated, it was found that the conversion of the desired products is less than 10%. However, such a yield is economically unacceptable.

DE-A 29 12 489 describes the preparation of carboxylic esters by hydroformylation of internal olefins which carry not more than 20 carbon atoms in the presence of a cobalt catalyst under from 150 to 300 bar.

It is a further object of the invention to provide a process for the preparation of carboxylic acids and carboxylic esters from polymers which still carry a carbon—carbon double bond. Such a process should make it possible to obtain the desired products with good conversion and high selectivity.

We have found that these objects are achieved by the use, defined at the outset, of carboxylic esters of the formula I.

The present invention furthermore relates to fuel compositions which contain carboxylic esters of the formula I in an amount of from 10 to 5000 ppm, in particular from 100 to 2000 ppm.

The present invention also relates to lubricant compositions which contain carboxylic esters of the formula I in an amount of from 0.5 to 15, in particular from 0.5 to 10, % by weight.

The present invention also relates to a process for the preparation of carboxylic acids or carboxylic esters, according to which polymers which have at least 30 carbon atoms and carry at least one carbon–carbon double bond are reacted with carbon monoxide and water or alcohols in the presence of catalytic amounts of a metal or of a metal compound of groups 8 to 10 of the Periodic Table. In the process, the reaction pressure is from 50 to 600 bar.

According to the invention, carboxylic esters of the formula I in which $R^1$ has a number average molecular weight of from 500 to 2500, particularly preferably from 700 to 1500, are preferably used.

In general, $R^1$ is a hydrocarbon radical which is obtainable by polymerization of olefins, the polymerization being carried out in such a way that the chain termination leads to a double bond (for example, by cationic or coordinate polymerization). These olefins are in general $C_2$–$C_{30}$-olefins, preferably $C_2$–$C_6$-olefins, particularly preferably $C_2$–$C_4$-olefins, among these in turn isobutene being particularly preferred. Both homopolymers and copoly- mers, for example polymers of from 70 to 95 mol% of isobutene and from 5 to 30 mol% of 1-butene, are suitable. As a result of their preparation process, these polyolefins generally consist of a mixture of compounds of different molecular weights. The carboxylic esters used according to the invention may be obtained, for example, by the process stated in EP-A 0 148 592.

However, novel carboxylic esters are preferably prepared by the following process from polymers having at least 30 carbon atoms:

The polymers to be used as starting material carry at least 30 carbon atoms and at least one carbon–carbon double bond. Polymers having one carbon–carbon double bond are preferred. Preferred among these are hydrocarbon polymers which are composed of aliphatic monoolefins, such as ethylene, propylene, n-butene, isobutene, hexene or mixtures of these monomers. The molecular weights are as a rule from 450 to 7000. Polypropenes and polyisobutenes which in general have molecular weights of from 450 to 3000, preferably from 700 to 1200, are particularly preferred. Such compounds are obtainable, for example, according to EP-A 481 297. Propene oligomers may be obtained, for example, according to Chem. Lett. (1991), 1525.

Catalysts used in the novel process are metals or metal compounds of groups 8 to 10 of the Periodic Table. These may be used as heterogeneous or, preferably, homogeneous catalysts. Examples of suitable metal compounds are the chlorides, acetates and nitrates of the stated metals, but the metals may also be used in elemental form. Cobalt, palladium and rhodium are preferred, as well as compounds thereof. Cobalt carbonyl compounds and cobalt salts are particularly preferred.

Carbon monoxide is used in excess in the reaction. The ratio of carbon monoxide to the polymer is established by means of the partial pressure of the carbon monoxide.

The polymer is reacted with carbon monoxide and with water or an alcohol. These alcohols are as a rule primary or secondary aliphatic $C_1$–$C_{20}$-alcohols, such as methanol, ethanol, isopropanol, n-propanol, n-butanol and 2-ethylhexanol, and $C_2$–$C_{30}$-amino-alcohols, such as 2-dimethylaminoethanol, 2-diethylaminoethanol, 2-diisopropylaminoethanol, 3-dimethylamino-1-propanol, 3-diethylamino-1-propanol, 3-diisopropylamino-1-propanol, 1-dimethylamino-2-propanol, 1-diethylamino-2-propanol, 1-diisopropyl-amino-2-propanol and 3-dimethylamino-1,2-propanediol, araliphatic $C_7$–$C_{12}$-alcohols, such as benzyl alcohol, aromatic $C_6$–$C_{10}$-alcohols, such as phenol, and $C_2$–$C_{20}$-mono- and polyalkylene glycols and monoethers, such as ethylene glycol, ethylene glycol monomethyl ether and diethylene glycol, diethylene glycol monomethyl ether, triethylene glycol, triethylene glycol monomethyl ether, tetraethylene glycol and tetraethylene glycol monomethyl ether. In general, from 1 to 30, preferably 10 to 25, mol of water or alcohol are use per mol of polymer compound. A reaction with water leads to the corresponding acid, while a reaction with alcohols leads to the esters.

The novel process is preferably carried out in the presence of nitrogen-containing bases. Tertiary aromatic amines, such as pyridine or picolines, have proven particularly suitable. These bases may be used in a molar ratio of from 1:1 to 50:1, preferably from 2:1 to 15:1, based on the catalytically active metal.

As a rule, the molar ratio of the polymer to the catalytically active metal is from 2:1 to 50:1, preferably from 4:1 to 15:1.

The reaction can be carried out in a solvent. The solvents are in general polar solvents, such as acetone, and ethers, such as tetrahydrofuran, but also the alcohols or water occurring as reactants in the reaction. These solvents may also be used as a mixture with hydrocarbons, such as alkanes. The amount of the solvent is in general from 10 to 90% by weight, based on the total batch.

The reaction can be carried out at from 20° to 300° C., preferably from 100° to 200° C. The reaction pressure is from 50 to 600, preferably from 100 to 300, bar absolute pressure. The reaction times are in general from 5 to 48 hours. For carrying out the reactions, the reactants are mixed and then brought to the reaction temperature under CO pressure. Working up can be carried out in a manner known per se, by separating off the catalyst, distilling off the solvent and purifying the reaction product by chromatography.

The reaction can be carried out continuously or batchwise.

The novel process permits the preparation of the products with high selectivity of the addition reaction of the carbon monoxide and the water or the alcohol and with good conversion.

The novel use of esters of the formula I as fuel additives, in particular for gasoline engines, permits combination with known detergents, for example polyisobutylamines, as obtainable, for example, by hydroformylation of polyisobutene, followed by reductive amination, and dispersants as the carrier oil components or as the sole detergent components.

Used as lubricant additives, the compounds of the formula I may also be used in combination with further conventional additives, for example corrosion inhibitors, antiwear additives, detergents, antioxidants and pour point improvers.

The detergent component used in the mixture with the novel substances can in principle be any known product suitable for this purpose, as described, for example, in J. Falbe and U. Hasserodt, Katalysatoren, Tenside und Mineralöladditive, G. Thieme Verlag, Stuttgart 1978, page 221 et seq. or in K. Owen, Gasoline and Diesel Fuel Additives, John Wiley & Sons, 1989, page 23 et seq.

N-containing detergents, for example compounds which contain an amino or amido group, are preferably used. Polyisobutylamines according to EP-A-0 244 616, ethylene-diaminetetraacetamides and/or -imides according to EP-A-0 188 786 or polyetheramines according to EP-A-0 244 725 are particularly suitable, reference being made to the definitions in these publications. As a result of their preparation, the products described there likewise have the advantage of being chlorine- or chloride-free.

The novel carboxylic esters may also be combined with conventional carrier oils. Particularly suitable carrier oils are those based on polyglycol, for example corresponding ethers and/or esters, as described in U.S. Pat. No. 5,004,478 or DE-A-38 38 918. Polyoxyalkylenemonools having terminal hydrocarbon groups (U.S. Pat. No. 4,877,416) or carrier oils as disclosed in DE-A-41 42 241 may also be used.

Suitable fuels for gasoline engines are leaded and in particular unleaded regular and premium gasoline. The gasolines may also contain components other than hydrocarbons, for example alcohols, such as methanol, ethanol or tert-butanol, and ethers, eg. methyl tert-butyl ether. In addition to the novel additives, the fuels also contain, as a rule, further additives, such as corrosion inhibitors, stabilizers, antioxidants and/or further detergents.

Corrosion inhibitors are generally ammonium salts of organic carboxylic acids which tend to form films because the starting compounds have an appropriate structure. Furthermore, amines for lowering the pH are frequently present in corrosion inhibitors. Heterocyclic aromatics are generally used for preventing corrosion of nonferrous metals.

Even in a small dose, the novel carboxylic esters make a large contribution to the overall performance of an additive package with regard to detergency. This makes it possible in general to save detergents, and the use of further additional detergents may even be superfluous in specific cases.

EXAMPLE 1

Preparation of methyl polyisobutanecarboxylate 900 g of polyisobutene (molecular weight 1100; 0.82 mol), 19.2 g of dicobalt octacarbonyl (56 mmol), 168 g of 3-picoline (1.8 mol), 600 g of methanol (18.8 mol) and 900 g of a $C_{10}$–$C_{13}$-alkane mixture were initially taken in an autoclave. CO was forced in to a pressure of 50 bar. The autoclave was heated to 180° C. and the CO pressure was increased to 270 bar. After 24 hours, air was passed in in order to remove the catalyst, the solvent and the picoline were separated off by distillation, and 920 g of a viscous product containing 71% of methyl polyisobutanecarboxylate remained. The conversion was 80% and the selectivity 89%. With pentane as solvent, the ester could be separated from the unconverted starting material by chromatography over silica gel.

Engine tests

EXAMPLE 2

In Examples 2a and 2b, dimethylaminoethyl polyisobutanecarboxylate, which was prepared starting from polyisobutene having a number average molecular weight of 1000 by a method similar to that of Example 1 using dimethylaminoethanol instead of methanol or by transesterification of methyl polyisobutanecarboxylate with dimethylaminoethanol, was tested as a fuel additive in engine tests.

The engine tests were carried out in an Opel Kadett 1.2 l engine according to CEC F/04/A/87. Fuel used: unleaded European premium grade.

The dose of dimethylaminoethyl polyisobutanecarboxylate and the results obtained are shown in the table.

TABLE

| Example | Dose [ppm] | Intake valve deposits [mg]*) Valves | | | |
|---|---|---|---|---|---|
| | | 1 | 2 | 3 | 4 |
| 2a | 400 | 15 (278) | 0 (132) | 3 (191) | 0 (180) |
| 2b | 200 | 22 (278) | 7 (132) | 10 (191) | 1 (180) |

*)Values in brackets: deposits without introduction of additive; the different values are due to differences in the unleaded European premium grade used.

EXAMPLE 3

In Examples 3a and 3b, methyl polyisobutanecarboxylate which was prepared according to Example 1 was tested as a fuel additive in engine tests.

The engine tests were carried out in an Opel-Kadett 1.2 l engine according to CEC F/04/A/87. Fuel used: unleaded European premium grade.

The dose of methyl polyisobutanecarboxylate and the results obtained are shown in the table.

TABLE

| Example | Dose [ppm] | Intake valve deposits [mg]*) Valves | | | |
|---|---|---|---|---|---|
| | | 1 | 2 | 3 | 4 |
| 3a | 400 | 4 (210) | 0 (150) | 6 (154) | 6 (200) |
| 3b | 200 | 16 (278) | 0 (132) | 2 (191) | 8 (180) |

*)Values in brackets: deposits without introduction of additive; the different values are due to differences in the unleaded European premium grade used.

We claim:

1. A process for introducing additives into fuels, wherein carboxylic esters of the formula I

$$R^1\text{—CO—O—}R^2 \quad\quad (I)$$

where $R^1$ is an aliphatic, straight-chain or branched hydrocarbon radical having alkyl side chains and a number average molecular weight of from 250 to 5000 and $R^2$ is a straight-chain or branched hydrocarbon radical of 1 to 30 carbon atoms or a radical of the formula II

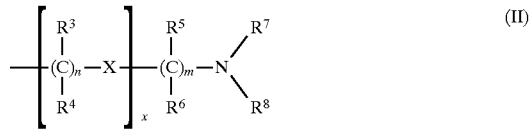

where $R^3, R^4, R^5$ and $R^6$, independently of one another, are each hydrogen, branched or straight-chain alky, an aromatic radical or an araliphatic radical which may also contain heteroatoms, $R^7$ and $R^8$, independently of one another, are each branched or straight-chain alkyl or an aromatic or araliphatic radical which may also contain heteroatoms, X is O, S, $NR^9$ or $PR^9$, where $R^9$ is an aliphatic or aromatic radical, n and m, independently of one another, are each from 2 to 20, and x is from 0 to 30, which have been prepared by reacting the corresponding polymers forming the basis of $R^1$ and having at least one carbon—carbon double bond with carbon monoxide and with alcohols of the formula $R^2$—OH in the presence of catalytic amounts of a metal or of a metal compound of groups 8 to 10 of the Periodic Table and in the presence of a nitrogen-containing base at from 50 to 600 bar, are introduces as additives.

2. The process defined in claim 1, wherein $R^1$ has a number average molecular weight of from 500 to 2500.

3. A fuel composition which contains of from 10 to 5000 ppm of a carboxylic ester of the formula I

where $R^1$ is an aliphatic, straight-chain or branched hydrocarbon radical having alkyl side chains and a number average molecular weight of from 250 to 5000 and $R^2$ is a straight-chain or branched hydrocarbon radical of 1 to 30 carbon atoms or a radical of the formula II

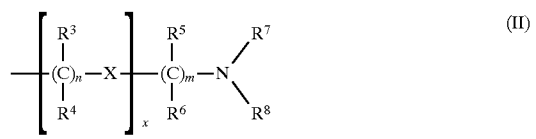

where $R^3, R^4, R^5$ and $R^6$, independently of one another, are each hydrogen, branched or straight-chain alkyl, an aromatic radical or an araliphatic radical which may also contain heteroatoms, $R^7$ and $R^8$, independently of one another, are each branched or straight-chain alkyl or an aromatic or araliphatic radical which may also contain heteroatoms, X is O, S, $NR^9$ or $PR^9$, where $R^9$ is an aliphatic or aromatic radical, n and m, independently of one another, are each from 2 to 20, and x is from 0 to 30, which have been prepared by reacting the corresponding polymers forming the basis of $R^1$ and having at least one carbon—carbon double bond with carbon monoxide and with alcohols of the formula $R^2$—OH in the presence of catalytic amounts of a metal or of a metal compound of groups 8 to 10 of the Periodic Table and in the presence of a nitrogen-containing base at from 50 to 600 bar.

4. The process defined in claim 1 wherein the carboxylic esters have been prepared from polyisobutene as the corresponding polymer forming the basis of $R^1$.

5. The process defined in claim 1 wherein the carboxylic esters have been prepared from polypropene or polyisobutene as the corresponding polymer forming the basis of $R^1$.

6. The process defined in claim 5 wherein the polypropene or polyisobutene has a molecular weight of from 450 to 3000.

* * * * *

UNITED STATES PATENT AND TRADEMARK OFFICE
CERTIFICATE OF CORRECTION

PATENT NO.: 5,876,467

DATED: March 2, 1999

INVENTOR(S): HOEHN et al.

It is certified that error appears in the above-identified patent and that said Letters Patent is hereby corrected as shown below:

Col. 6, claim 1, line 60, "alky" should be --alkyl--.

Signed and Sealed this

Twentieth Day of July, 1999

Attest:

Q. TODD DICKINSON

Attesting Officer

Acting Commissioner of Patents and Trademarks